(12) United States Patent
Thorsen (10) Patent No.: US 11,528,919 B2
(45) Date of Patent: Dec. 20, 2022

(54) METHOD OF CLEANING A HIGH TEMPERATURE FOOD PROCESSING LINE IN PLACE AND FOOD STERILIZATION LINE

(71) Applicant: SPX FLOW TECHNOLOGY DANMARK A/S, Silkeborg (DK)

(72) Inventor: Claus Thorsen, Silkeborg (DK)

(73) Assignee: SPX Flow Technology Danmark A/S, Silkeborg (DK)

(*) Notice: Subject to any disclaimer, the term of this patent is extended or adjusted under 35 U.S.C. 154(b) by 474 days.

(21) Appl. No.: 16/061,374

(22) PCT Filed: Dec. 19, 2016

(86) PCT No.: PCT/EP2016/081789
§ 371 (c)(1),
(2) Date: Jun. 12, 2018

(87) PCT Pub. No.: WO2017/103276
PCT Pub. Date: Jun. 22, 2017

(65) Prior Publication Data
US 2018/0352823 A1 Dec. 13, 2018

(30) Foreign Application Priority Data
Dec. 18, 2015 (DK) .............................. PA201500819

(51) Int. Cl.
*A23C 7/02* (2006.01)
*A23C 3/033* (2006.01)
(Continued)

(52) U.S. Cl.
CPC ............... *A23C 7/02* (2013.01); *A23C 3/033* (2013.01); *A23L 2/46* (2013.01); *A61L 2/07* (2013.01);
(Continued)

(58) Field of Classification Search
CPC ......... A23C 7/02; A23C 3/033; B08B 9/0321; B08B 9/0325; A61L 2/07; A61L 2/18; A61L 2202/17; A23L 2/46
See application file for complete search history.

(56) References Cited

U.S. PATENT DOCUMENTS

| | | | | |
|---|---|---|---|---|
| 3,041,185 A | * | 6/1962 | Martin | .................... B65B 55/18 |
| | | | | 426/232 |
| 2003/0049356 A1 | * | 3/2003 | Nielsen | ................... A23L 3/003 |
| | | | | 426/522 |

(Continued)

FOREIGN PATENT DOCUMENTS

| EP | 2772319 A1 | 9/2014 |
|---|---|---|
| JP | 2013091018 A | 5/2013 |

(Continued)

OTHER PUBLICATIONS

International Search Report from PCT/EP2016/081789; dated Apr. 6, 2017.

*Primary Examiner* — Regina M Yoo
(74) *Attorney, Agent, or Firm* — IceMiller LLP (57) ABSTRACT

A high temperature food treatment method is disclosed wherein by alternatingly operating between a first final heater (13) and second final heater (23) arranged in parallel on a food processing line (30, 40, 50), it is possible to operate a continuous process, yet significantly reducing the overall downtime of the processing line (30, 40, 50), by performing a cleaning in place process on the final heater (13, 23), not currently being used in the high temperature food treatment process, thereby eliminating or significantly reducing the influence on the processing line (30, 40, 50) downtime by the process elements and/or processing equipment most easily contaminated.

6 Claims, 7 Drawing Sheets

(51) Int. Cl.
    *A23L 2/46*   (2006.01)
    *A61L 2/18*   (2006.01)
    *B08B 9/032*  (2006.01)
    *A61L 2/07*   (2006.01)

(52) U.S. Cl.
    CPC .............. *A61L 2/18* (2013.01); *B08B 9/0321* (2013.01); *B08B 9/0325* (2013.01); *A61L 2202/17* (2013.01)

(56) References Cited

U.S. PATENT DOCUMENTS

| | | | | |
|---|---|---|---|---|
| 2004/0187707 | A1* | 9/2004 | Nielsen | A23L 3/20 99/453 |
| 2005/0031751 | A1* | 2/2005 | Weng | A23L 3/18 426/521 |
| 2005/0233041 | A1 | 10/2005 | Wilken et al. | |
| 2011/0083752 | A1* | 4/2011 | Wu | A61L 2/04 137/15.01 |
| 2016/0052767 | A1* | 2/2016 | Eaton | B67C 3/16 141/9 |

FOREIGN PATENT DOCUMENTS

| | | |
|---|---|---|
| WO | 1993/05667 A1 | 4/1993 |
| WO | 2004/077968 A1 | 9/2004 |

\* cited by examiner

METHOD OF CLEANING A HIGH TEMPERATURE FOOD PROCESSING LINE IN PLACE AND FOOD STERILIZATION LINE

CROSS-REFERENCE TO RELATED PATENT APPLICATIONS

The present application is a National Stage of International Patent Application No. PCT/EP2016/081789, filed Dec. 19, 2016, entitled "Method of Cleaning a High Temperature Food Processing Line in Place and Food Sterilization Line" and claims the priority of Danish Patent Application No. PA201500819, filed on Dec. 18, 2015, the disclosures of which are incorporated herein by reference in their entirety.

FIELD

The present invention relates to the field of processing food and in particular to a method of cleaning a high temperature food processing line in place. Further the invention describes a high temperature food processing line configured to permit execution of the inventive method.

BACKGROUND

In the field of food processing, food product sterilization by heat treatment is a recurrent subject. The aim of food product sterilization by heat treatment is the reduction the number of microbiological entities or micro-organisms, such as e.g. bacteria, spores, yeast, mold, or bacteriophages. In particular, the removal of pathogens from the food product being heat treated is of particular importance.

Modern food product processing plants are designed to reduce contamination within the processing lines through which the food product to be processed is transported. Important elements in this design is the use of low fouling and/or easy to clean and maintain materials such as e.g. stainless steel, but also designing the processing lines, process elements, and processing equipment to allow cleaning-in-place (CIP), i.e. the cleaning of the processing lines, process elements and processing equipment without having to take the equipment and processing lines apart.

The present invention is concerned with improvements in methods for cleaning-in-place and processing lines optimized for use with the improved methods. Throughout the present disclosure, cleaning-in-place, CIP, and/or cleaning in place, are used interchangeably without preference. In general, the skilled person is aware of adequate methods of cleaning in place responsive to a particular type of food product and such methods are in general outside the scope of the present disclosure. Nevertheless, when performing a CIP-procedure according to the invention as detailed below on a food sterilization line, it is necessary (and legally mandatory) that the CIP-procedure is a sterilization in place procedure as are known in the art.

A recurring problem when cleaning in place is that the same food product contaminates different processing equipment differently in a processing line comprising a given sequence of process elements through which the food product is transported. For example, in a sequence of process elements comprising a low temperature heat exchanger and a high temperature heat exchanger, e.g. a pre-heater and a final heater; the low temperature heat exchanger will normally become contaminated differently from the high temperature heat exchanger, e.g. by milk passing through the sequence of processing elements, with the high temperature heat exchanger usually becoming the most contaminated, e.g. due to stronger burning of the milk on the high temperature heat exchanger surfaces than on the low temperature heat exchanger surfaces.

Throughout the present disclosure, a distinction will be made between process elements and processing equipment, wherein all processing equipment will be considered processing elements, but not all process elements are to be considered processing equipment. An example of a processing element, which is also processing equipment could be a heat exchanger. A heat exchanger acts in a process by acting on another element of the process and therefore it is both a processing element and processing equipment, whereas e.g. by valves are process elements but not processing equipment as valves acts in the process but do not act on other elements of the process.

When cleaning in place of the exemplary sequence of process elements described above, the overall time to clean the sequence of process elements in place will be normally be determined by the time necessary to clean the most contaminated piece of processing equipment. And, while a sequence of process elements can be designed to allow each element of processing equipment to be decontaminated independently, the processing line remains at a standstill for at least the time necessary to clean the processing equipment having the longest cleaning time.

This is highly disadvantageous as processing equipment having shorter cleaning times will be ready for use, yet standing idle, while the processing equipment having the longest cleaning time is being finally cleaned. In particular, where some processing equipment is only minimally contaminated at the time when the most contaminated processing equipment is in need of cleaning; unnecessary processing equipment downtime, and if the processing line is so constructed also unnecessary processing equipment cleaning, constitutes a problem.

The present inventors have now surprisingly discovered that this problem can be overcome, or at least significantly reduced, by following the methods disclosed herein.

SUMMARY OF THE INVENTION

In accordance with the detailed disclosure presented below, the objects of the present invention have been solved by providing methods and production lines as detailed in this summary and in detail in the detailed description.

According to a first aspect and embodiment there is herein disclosed a method of operating a food processing line (30,40,50,60,70) during a cleaning-in-place procedure while converting a matter flow of a pumpable food product (11) into a treated product (15) in a food treatment process; said food processing line (30,40,50,60,70) comprising: a plurality of operatively, sequentially arranged and fluidly connected process elements (12,13,23,14); wherein at least a first and a second substantially alike process elements (13, 23) of said plurality of process elements are arranged in parallel on, respectively, a first sequence (I) and a parallel sequence (III) of process elements on said food processing line (30), such that said first sequence (I) comprising said first substantially alike process element (13) can be valved (133,135) off from or opened to said food processing line (30), when said parallel sequence (III) comprising said second substantially alike process element (23), respectively is oppositely valved (233,235) off from or opened to said food processing line (30); wherein each of said two sequences (I,III) comprises inlet valves (134,234) and outlet valves (136,236) arranged around all process elements (13, 23) on a sequence (I;III) for permitting cleaning agents for use in a cleaning-in-place procedure entry to and exit from a respective sequence (I, III), while a said respective sequence (I, III) is valved off from said food processing line (30); and wherein a said sequence (I, III) respectively diverts from and reunites to said food processing line (30,40,50,60, 70) at said inlet (133,233) and outlet valves (135,235); said method comprising: a) prior to executing a food treatment process on said food processing line (30), valving off (233,235) from said food processing line (30) said parallel sequence (III) of process elements, and leaving said first sequence (I) of process elements open (133,135) for passage of a matter flow of said food product (11); b) executing said food treatment process on said food processing line (30) thereby converting said food product (11) into a treated product (15) in said food treatment process; c) after a time period of executing said food treatment process switching, concurrently during execution of said food treatment process, said matter flow from passage of said first sequence (I) to passage of said parallel sequence (III), thereby replacing said first sequence (I) by said parallel sequence (III) in said food processing line (30), by valving off (133,135) said first sequence (I) from said food processing line (30) and concurrently opening (233,235) said parallel sequence (III) to said food processing line (30); and d) while said first sequence (I) is valved off from said food processing line (30) executing a cleaning-in-place procedure on said first sequence (I).

Further, there is herein disclosed a method according a second embodiment of the first aspect, wherein steps c) and d) are repeated until said food processing line (30,40,50,60, 70) is halted and/or said food treatment process is terminated.

Further, there is herein disclosed a method according a third embodiment of the first aspect, wherein said first and said substantially alike second process elements of said plurality of process elements (13,23) are a first final heater (13) and a second final heater (23).

Further, there is herein disclosed a method according a fourth embodiment of the first aspect, wherein said first final heater (13) and said second final heater (23) are both direct steam heaters.

Further, there is herein disclosed a method according a fifth embodiment of the first aspect, wherein said final heaters (13a, 23a) are augmented, independently, with a holding cell (13b, 23b).

Further, there is herein disclosed a method according a sixth embodiment of the first aspect, wherein said food processing line (30,40,50,60,70) further comprises at least one preheater (12,32) arranged on said food processing line (30,40,50,60,70) before said first and said parallel sequences (I,III) divert from said food processing line.

Further, there is herein disclosed a method according a seventh embodiment of the first aspect, wherein said food processing line (30,40,50,60,70) further comprises at least one cooler (14,44,54) arranged on said food processing line (30,40,50,60,70) after said first and said parallel sequences (I,III) have reunited with said food processing line.

Further, there is herein disclosed a method according an eighth embodiment of the first aspect, wherein said cooler (14) is a flash cooler (14) or a flash cooler (14) augmented with one or more indirect coolers (441,541,542).

Further, there is herein disclosed a method according a ninth embodiment of the first aspect, wherein a filling station (45,55) is the last process element arranged on said food processing line (40,50).

Further, there is herein disclosed a method according a tenth embodiment of the first aspect, wherein a feed tank (41,51) is the first process element arranged on said food processing line (40,50).

Further, there is herein disclosed a method according an eleventh embodiment of the first aspect, wherein said valves (133,233) and/or said valves (135,235) have been combined, pair wise, into a single, three-way valve (58).

Further, there is herein disclosed a method according a twelfth embodiment of the first aspect, wherein said food processing line (30,40,50,60,70) is a heat treatment food processing line for pasteurizing or sterilizing a liquid food product (11).

Further, there is herein disclosed a method according a thirteenth embodiment of the first aspect, in said food processing line (30,40,50,60,70), said food product (11) is first submitted to preheating in a preheater (12) and subsequently submitted to a high temperature treatment in either of said first or said parallel sequences (I,III).

Further, there is herein disclosed a method according a fourteenth embodiment of the first aspect, wherein said food product (11) is first submitted to a pasteurizing temperature in a preheater (12,32) and subsequently submitted to a sterilizing, high temperature treatment above 120° C. in respectively said first or parallel sequences (I,III).

According to a second aspect and embodiment there is herein disclosed a method of operating a food sterilization line (30,40,50,60,70) during a cleaning-in-place procedure while converting a matter flow of a pumpable food product (11) into a sterilized product (15) in a food sterilization process; said food sterilization line (30,40,50,60,70) comprising: a plurality of operatively, sequentially arranged and fluidly connected process elements (12,13,23,14) comprising a first and second direct steam heater (13,23) for sterilizing a pumpable food product (11) at a temperature between 120° C. and 160° C. arranged in parallel on, respectively, a first sequence (I) and a parallel sequence (III) of process elements on said food sterilization line (30,40, 50,60,70), such that said first sequence (I) comprising said first direct steam heater (13) can be valved (133,135) off from or opened to said food sterilization line (30,40,50,60, 70), when said parallel sequence (III) comprising said second direct steam heater (23), respectively is oppositely valved (233,235) off from or opened to said food sterilization line (30,40,50,60,70); wherein each of said two sequences (I,III) comprises inlet valves (134,234) and outlet valves (136,236) arranged around all process elements (13, 23) on a sequence (I;III) for permitting cleaning agents for use in a cleaning-in-place procedure entry to and exit from a respective sequence (I,III), while a said respective sequence (I,III) is valved off from said food sterilization line (30,40,50,60,70); and wherein said respective sequences (I,III) divert from and reunite to said food sterilization line (30) at said respective inlet (133,233) and outlet valves (135,235); said method comprising: a) prior to executing a food sterilization process on said food sterilization line (30,40,50,60,70), valving off (233,235) from said food sterilization line (30,40,50,60,70) said parallel sequence (III) of process elements, and leaving said first sequence (I) of process elements open (133,135) for passage of a matter flow of said food product (11); b) executing said food sterilization process on said food sterilization line (30,40, 50,60,70), by operating said first and second direct steam heater (13,23) at a temperature between 120° C. and 160° C., thereby converting said food product (11) into a sterilized product (15) in said food sterilization process; c) after a time period of executing said food sterilization process switching, concurrently during execution of said food sterilization process, said matter flow from passage of said first sequence (I) to passage of said parallel sequence (III), thereby replacing said first sequence (I) by said parallel sequence (III) in said food sterilization line (30,40,50,60,70), by valving off (133,135) said first sequence (I) from said food sterilization line (30) and concurrently opening (233,235) said parallel sequence (III) to said food sterilization line (30); and d) while said first sequence (I) is valved off from said food sterilization line (30,40,50,60,70) executing a cleaning-in-place procedure on said first sequence (I).

Further, there is herein disclosed according to a second embodiment of the second aspect, a method of operating a food sterilization line (30,40,50,60,70) during a cleaning-in-place procedure, wherein said first and second direct steam heater (13,23) are operated at a temperature between 120° C. and 160° C. for a time between 0.5 to 10 seconds while sterilizing said pumpable food product (11).

Further, there is herein disclosed according to a third embodiment of the second aspect, a method of operating a food sterilization line (30,40,50,60,70) during a cleaning-in-place procedure, wherein said first and second direct steam heaters (13,23) comprises a combination of a direct steam heater (13a,23a) with a holding cell (13b,23b).

Further, there is herein disclosed according to a fourth embodiment of the second aspect, a method of operating a food sterilization line (30,40,50,60,70) during a cleaning-in-place procedure, wherein the heating time in the direct steam heater (13a,23a) is less than 2 seconds and the holding time in the holding cell (13b,23b) is between 1 second to about 10 seconds.

Further, there is herein disclosed according to either the first or the second aspect, a method wherein said pumpable food product (11) is a milk, a milk derivative, a juice, a vegetable liquid food product, a soy milk, a soup, and/or a dessert.

According to a third aspect and embodiment there is herein disclosed a food sterilization line (40,50), said food sterilization line (40,50) comprising: a plurality of operatively, sequentially arranged and fluidly connected process elements (42,52,13,23,44,54) comprising a first and second direct steam heater (13,23) for sterilizing a pumpable food product (11) at a temperature between 120° C. and 160° C. and operatively arranged in parallel on, respectively, a first sterilizing sequence (I) and a parallel sterilizing sequence (III) of process elements on said food sterilization line (40,50), such that said first sequence (I) comprising said first direct steam heater (13) can be valved (133,135) off from or opened to said food sterilization line (40,50), when said parallel sequence (III) comprising said second direct steam heater (23), respectively is oppositely valved (233,235) off from or opened to said food processing line (30); wherein each of said two sequences (I,III) comprises inlet valves (134,234) and outlet valves (136,236) arranged around all process elements (13,23) on a sequence (I;III) for permitting cleaning agents for use in a cleaning-in-place procedure entry to and exit from a respective sequence (I,III), while a said respective sequence (I,III) is valved off from food sterilization line (40,50); wherein said respective sequences (I,III) divert from and reunite to said food sterilization line (40,50) at said respective inlet (133,233) and outlet valves (135,235); said food sterilization line (40,50) further comprising: a pre-heater (42,52) operatively arranged on said food sterilization line (40,50) upstream from said sequences (I,III) before said sequences divert from said food sterilization line (40,50); and a flash cooler (44,54) operatively arranged on said food sterilization line (40,50) downstream from said sequences (I,III) after said sequences reunite with said food sterilization line (40,50); characterized in that: when one sequence (I,III) is available as an operative sterilizing sequence for the food sterilization process, the other sequence (I,III) is not available as an operative sterilizing sequence for the food sterilization process.

Further, there is herein disclosed according to a second embodiment of the third aspect, a food sterilization line (40,50) further comprising a feed tank (41,51) operatively arranged on said food sterilization line (40,50) upstream from said pre-heater (42,52).

Further, there is herein disclosed according to a third embodiment of the third aspect, a food sterilization line (40,50) further comprising a filling station (45,55) arranged at a downstream end of said food sterilization line (40,50).

Further, there is herein disclosed according to a fourth embodiment of the third aspect, a food sterilization line (40,50) further comprising at least one indirect cooler (441, 541,542) arranged on said food sterilization line (40,50) after said flash cooler (44,54) and before, when present, said filling station (45,55).

Further, there is herein disclosed according to a fifth embodiment of the third aspect, a food sterilization line (40,50) further comprising a controller for executing a method according to any of the first and second aspects and embodiments thereof.

DETAILED DESCRIPTION

In the heat treatment of food products such as e.g. milk products, juices, or soups, in particular in the sterilization of food products; it is a recurrent problem that the food products will foul the process elements thereby building up layers of debris on the processing elements. Food sterilization processes, e.g., are in particular sensitive to temperature and processing equipment operating at a higher temperature, e.g. above 100° C., in general will foul more and faster at a given flow rate of the food product through a processing plant comprising a food product heat treatment line than processing equipment operating at a lower temperature.

Figure 1:
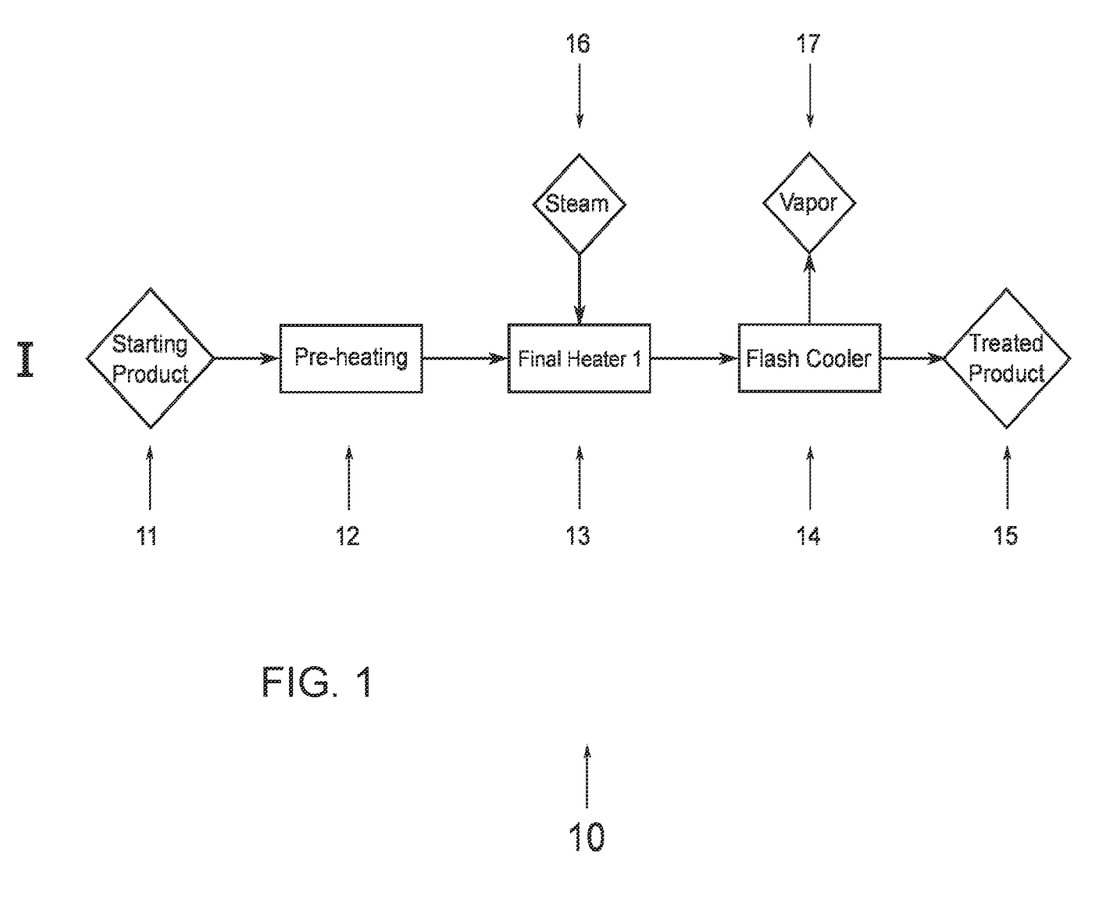
FIG. 1: Prior art high temperature food processing line

FIG. 1 details a typical prior art processing line (10) for heat treating a pumpable food product, e.g. for pasteurizing, for ultrahigh temperature treatment (UHT-treatment), and/or for sterilizing. This process is e.g. exemplified in WO 2004/077968. In the process displayed, a food product (11) is subjected to pre-heating in a pre-heater (12) upon which it is heated to a sterilizing temperature in a first final heater (13) upon which it is cooled in a (flash) cooler (14) to yield a heat treated product. The process of the figure (exemplified in WO 2004/077968 for juice treatment) utilizes a first final heater for infusion or injection heating (13) using steam (16)

and cooling in the form of flash cooling (14) with the concomitant withdrawal of vapor (17) to yield the heat treated product (15).

Accordingly, the processing line (10) detailed in the figure comprises a sequence (I) of fluidly connected process elements (12,13,14) arranged sequentially and fluidly connected, e.g. by pipes, to allow passage by pumping of the food product (11) through the processing line (10) according to the requirements of the particular food heat treatment and/or sterilization process intended for this particular food product.

In order to transport the food product through the sequence (I) of fluidly connected process elements (12,13, 14) one or more food pumps will supply the necessary driving force for the desired matter transport. The skilled person, in the context of the present invention, is familiar with the requirements for adequately dimensioning and applying food pumps, such that for a given type of food and flow rate one or more food pumps can be applied at adequate positions along the aforementioned sequence (I) of fluidly connected process elements to adequately transport the food product (11) trough said sequence (I) of fluidly connected process elements to execute the desired heat treatment and/or sterilization process.

Hence, while it shall be understood that food pumps may be comprised in said sequence (I) of fluidly connected process elements, the details of such food pumps are considered outside the scope of the present invention, as being specific to a particular food product and method of heat treatment and/or sterilization process being executed in the sequence (I) of process elements.

Figure 2:
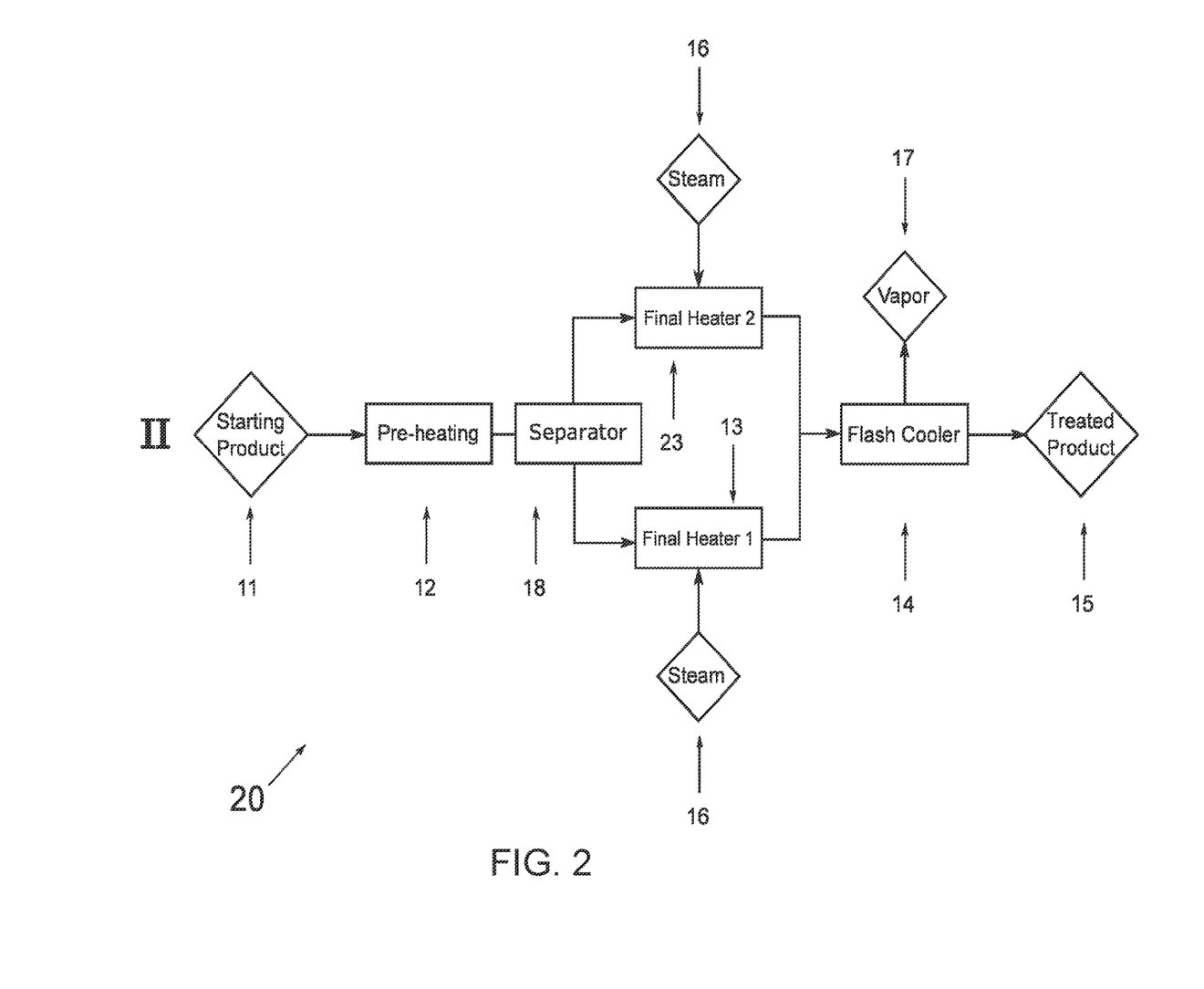
FIG. 2: Prior art high temperature food processing line

FIG. 2 details another prior art processing line (20) for heat treating a food product, e.g. for pasteurizing, for ultrahigh temperature treatment (UHT-treatment), and/or for sterilizing. This process is e.g. exemplified in WO 2004/077968. In the process displayed, a food product (11) is subjected to pre-heating (12) upon which it is separated in a separator (18) into two different product streams, and wherein each product stream is subsequently heated to a sterilizing temperature in two separate final heaters, a first final heater (13) and a second final heater (23); upon which the two product streams are either individually cooled (not shown) or combined and cooled in a flash cooler (14) to yield a heat treated product. Holding cells (not shown) are arranged after the final heaters, with holding cell heat treatment at the injector temperature for not longer than 1 sec.

The process of the figure (exemplified in WO 2004/077968 for juice treatment) utilizes a first and second final heater(s) arranged in parallel for infusion or injection heating (13) using steam (16) and cooling in the form of flash cooling (14) with the concomitant withdrawal of vapor (17) to yield the heat treated product (15). However, due to the separator (18) it is not possible to shut down either of the final heaters without shutting down the other also, and hence the entire production line, since material separated off and directed to a closed line would lead to failure of the overall process matter flow.

Accordingly, the processing line (20) detailed in FIG. 2 comprises a sequence (II) of fluidly connected process elements (12,13,23,14) arranged sequentially and fluidly connected, e.g. by pipes, to allow passage of the food product (11) through the processing line (20) according to the requirements of the particular food heat treatment and/or sterilization process intended for this particular food product; and wherein a first final heater (13) and a second final heater (23) has been arranged in parallel on the processing line (20).

In both the exemplified processing lines (10,20) of the prior art, the process elements labeled final heater 1 (13) and final heater 2 (23) in the figures, i.e. the first and second final heaters, are the most vulnerable to fouling by the food product being treated in the processing line due to these process elements operating at the highest temperatures. Hence the downtime of the processing lines (10,20) will be determined (mostly) by the need to maintain operation conditions of the final heaters (13,23), thereby leading to underutilization of the further process elements and/or processing equipment.

Even, such as in the process discussed in WO 2004/077968, where different food products are simultaneously heat treated, if only one of the final heaters is more vulnerable than its counterpart, it remains a considerable problem that the entire processing line (20) will have to cease operation; whenever the most vulnerable of the exemplified final heaters (13,23) are in need of cleaning due to fouling.

The present inventors have now surprisingly realized; that by operating a high temperature food treatment process alternatingly between a first final heater (13) and second final heater (23) arranged in parallel on a sequence (II) of process elements, it is possible to operate a continuous process, yet significantly reducing the overall downtime of the processing line, by performing a cleaning in place process on the final heater, not currently being used in the high temperature food treatment process, thereby eliminating or significantly reducing the influence on the processing line downtime by the process elements and/or processing equipment most easily contaminated.

Figure 3:
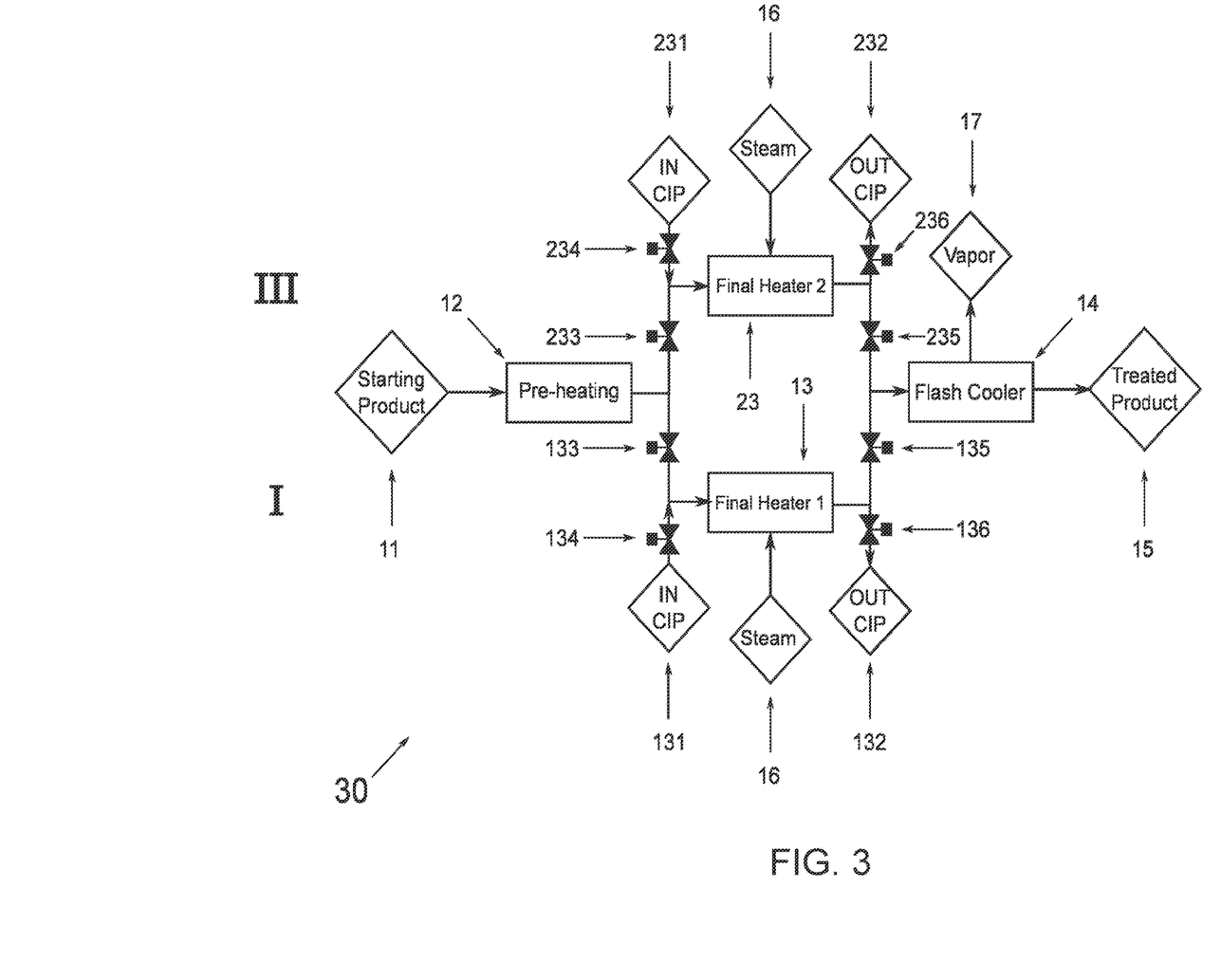
FIG. 3: High temperature food processing line of the invention

FIG. 3 details a processing line (30) arranged to execute the inventive method of the present disclosure.

A pumpable food product (11), preferably a pumpable, liquid food product, more preferably a milk, a milk derivative, a juice, a vegetable liquid food product, a soy milk, a soup, and/or a dessert and/or even most preferable, a milk derivative, is provided to the processing line (30), the processing line (30) comprising at least two sequentially and fluidly connected process elements (12,13,14). The food product is allowed to traverse, by pumping, the at least two sequentially and fluidly connected process elements (12,13, 14) to yield a treated product (15) after passage of the aforementioned processing line (30). Thereby a matter flow of the food product (11) is established through the processing line (30). In the exemplified processing line (30), the treatment process is a food sterilization process wherein the food product (11) is pre-heated in a pre-heater (12) to a first temperature and subsequently heated to a final processing temperature in a first final heater (13) upon which the food product; which has now become a heat treated product; is cooled in a cooler (14) to yield a desired treated product (15).

In the preferred embodiments, the first temperature is a pasteurizing temperature for the food product (11) to be processed in the food processing line (30), e.g. 75° C. for skimmed milk, and/or the final processing temperature is a sterilizing temperature, e.g. 146° C. for skimmed milk. In general, the skilled person will know how to determine pasteurizing and sterilizing temperatures for a given food product and the present invention is not limited by the actual temperatures a food product (11) will experience in a given food process executed on the food processing line (30) of the invention.

In the exemplified processing line (30) the first and second final heaters (13,23) of the exemplified embodiments are both operating by direct steam heating utilizing steam (16), either by injection (direct steam injection, DSI injection) or by infusion (direct steam infusion), both of which options are preferred. Further, in the exemplified processing line (30) the cooler (14) is a flash cooler (14) wherein surplus water from the cooling process is withdrawn as vapor (17). In general, direct steam heating is preferable over heat exchangers for establishing a sterilizing temperature in a food processing line due to reduced burning, and because the taste of the final product (15) will be closer to the taste of the initial food product (11) with reduced cooked taste.

Generally, it is contemplated, that when executing a food sterilization process according to the method of the invention, the operating temperatures of the direct steam heaters shall be between 120° C. to 160° C., preferably between 125° C. to 150° C., more preferably between 130° C. and 147° C., and most preferably between 135° C. to 144° C.

Further, it is contemplated that the total heating time at the sterilization temperatures shall be between 0.5 to 10 seconds, preferably 1 to 9 seconds, more preferably between 2 to 8 seconds, even more preferably between 3 to 7 seconds and most preferably between 4 to 6 seconds.

Figure 5:
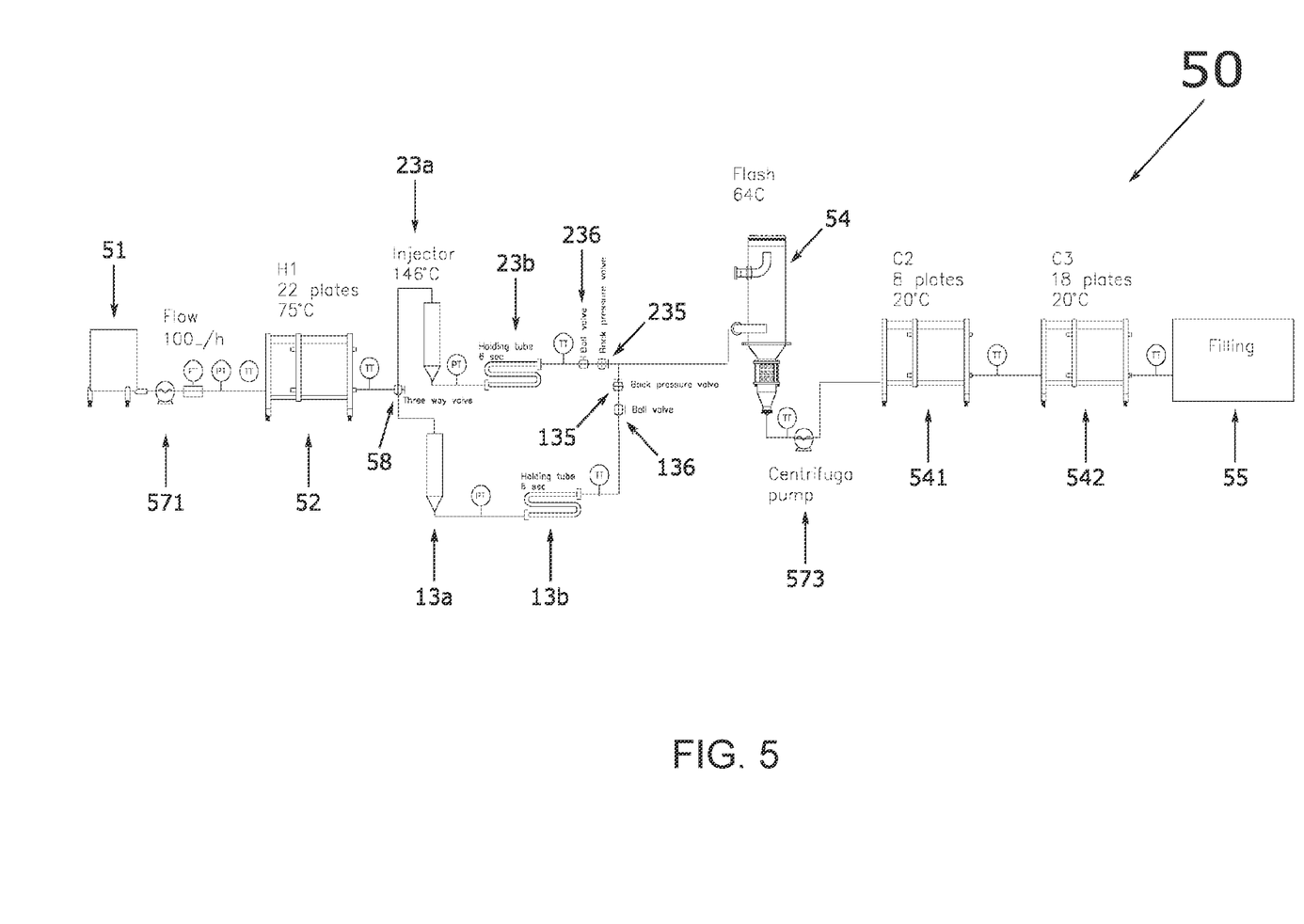
FIG. 5: High temperature milk sterilizing line of invention

In some embodiments, the final heaters (13,23) can be a combination of a direct steam heater (13a,23a) with a holding cell (13b,23b) (cf. FIG. 5). In this situation, it is preferable that the heating time in the direct steam heater is less than 2 seconds and the holding time in the holding cell is between 1 second to about 10 seconds.

The first final heater is arranged on a first sequence (I) of process elements further comprising at least two valves (133,135) arranged, respectively, at an entry point as an entry valve (133), and at an exit point as an exit valve (135) to the first sequence (I) of process elements, such that this first sequence (I) of process elements can be isolated from the further process elements (12,13) on the processing line (30), by closing off the two respective valves (133,135) at the entry and exit points to the aforementioned sequence (I).

Figure 4:
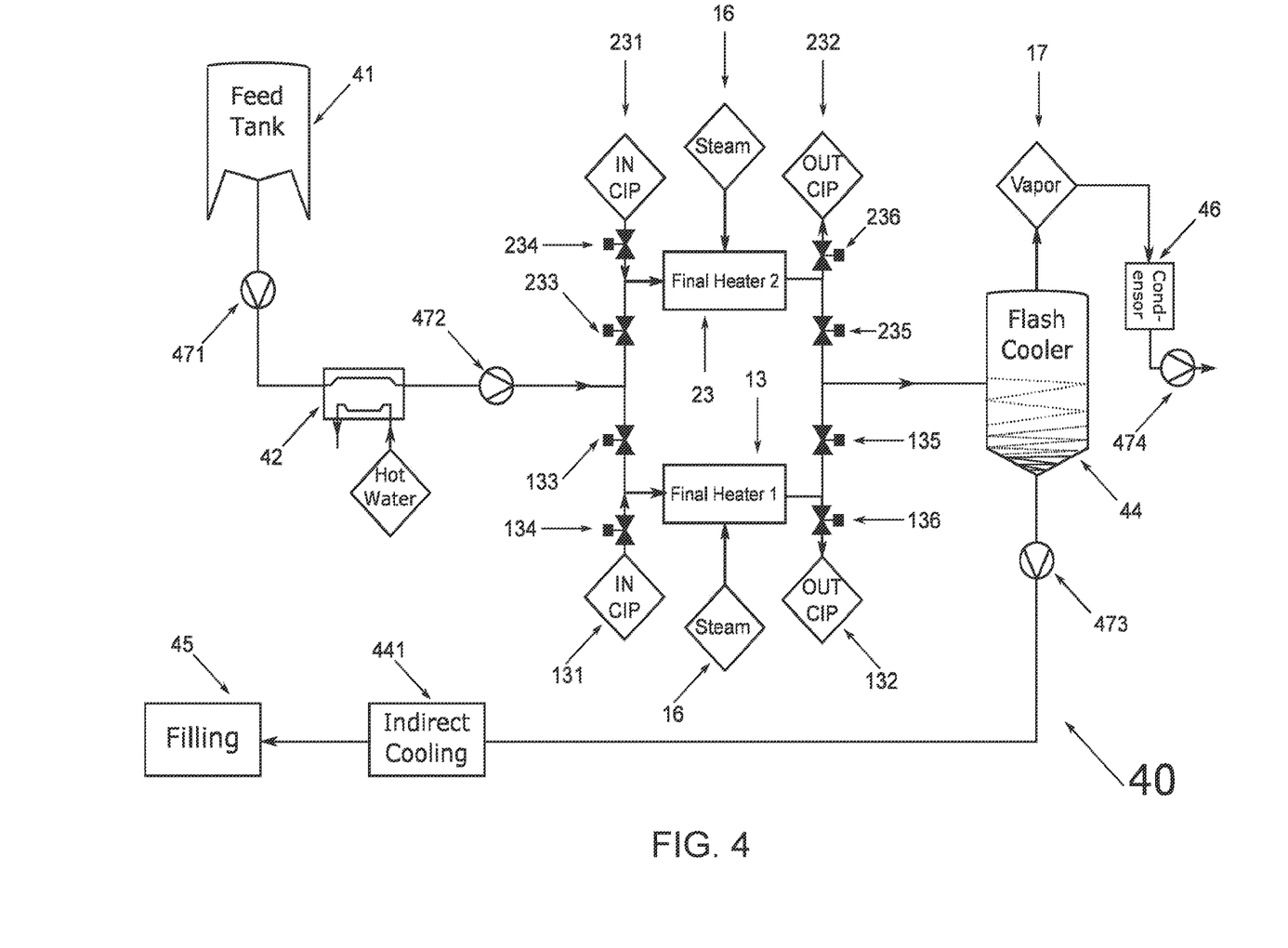
FIG. 4: Detailed high temperature food processing line of the invention

For clarity, the positions of pumps and other means for matter transport through the processing line (30) have been omitted from the drawing. A necessary number of pumps will have been applied along arriving or departing lines, such that the food product (11) can traverse a particular sequence of process element even when other sequences of process elements have been valved off from the aforementioned sequence. FIG. 4 details and exemplifies one possible embodiment of the generalized processing line (30) disclosed in FIG. 3, including the indication of suggested placements and numbers of valves and pumps.

In the exemplified processing line (30) of FIG. 3, the sequence (I) comprising the first final heater (13) is the process element and process equipment most vulnerable to contamination by the food product (11) during its passage of the aforementioned processing line (30) and sequence (I). The uptime of the processing line (30) therefore is determined by the time intervals between necessary cleaning of this process element (13).

A second final heater (23) has therefore been further provided in the processing line (30), and arranged in parallel with the aforementioned first final heater (13) on the aforementioned processing line (30), thereby forming a parallel sequence (III) of process elements. On the processing line (30), each sequence (I,III) of process elements has been provided with valves (133,135,233,235). Thereby, a respective sequence (I,III) of process elements can be valved off from its parallel counterpart during operation of the processing line (30). In parallel with the first sequence (I), the valves (233,235) have been arranged on the process line (30) respectively, at an entry point as an entry valve (233), and at an exit point as an exit valve (235) from the aforementioned parallel sequence (III).

In general, no particular emphasis is placed on the particular type of valve, which can be used with the present invention, for valving off a particular sequence (I,III) of the food processing lines of the invention. The important aspect for the invention is, that a particular sequence (I,III) can be reliably and, usually rapidly, coupled on and off the food processing line, during operation of the same food processing line.

It can be desirable, that the valves can rapidly close of a particular sequence (I,III) during operation of the food processing line (30) in order to avoid large pressure fluctuations in the production line. To this effect, it is particularly preferred that the downstream valves (135,235) are back-pressure valves.

A three-way valve (58) as exemplarily detailed in FIG. 5 for the upstream valves (133,233) can, pair wise, replace the paired valves (133,233) and (135,235).

However, as described below in relation to FIG. 5 and also above, it is generally preferably only to replace the upstream valves (133,233) by a single three-way valve (58), and let the valves (135,235) be backpressure valves, in order to assure proper functioning of the final direct steam injection heaters (13,23), and to avoid pressure surges in the system.

Each of the two sequences (I,III) of process elements have further been provided with CIP-entry valves (134,234) and CIP-exit valves (136,236) arranged between the aforementioned entry valves (133,233) and exit valves (135,235) on each respective sequence (I,III) of process elements. Thereby, a cleaning-in-place procedure can be implemented on a respective sequence (I,III) between two respective CIP-entry valves (134,234) and CIP-exit valves (136,236) corresponding to a given sequence (I,III) of process elements, when the respective sequence (I,III) has been valved off from the processing line (30) on which the mentioned sequences (I,III) have been arranged, by closing a respective entry valve (133,233) and exit valve (135,235).

In operation of the exemplary processing line (30) of FIG. 3, when implementing the exemplary food sterilization procedure mentioned above, the food product (11) is first subjected (after preheating) to the desired final heating step in the first final heater (13) by passing the food product (11) through the aforementioned first sequence (I) of process elements. During this final heating, the access for the food product (11) to the parallel sequence (III) of process elements is blocked, by closing the entry valve (233) and exit valve (235) comprised in the parallel sequence (III).

During the heating of the pumpable food product (11) in the first final heater (13), the heater becomes fouled and after a given time, which must be individually determined for each heating process and food product (11), the heater (13) has become so fouled by the process that it is considered necessary to perform a CIP-procedure on the fouled first final heater (13).

Rather now, than shutting down the entire processing line (30) for cleaning-in-place, only the first sequence (I) of process elements comprising the first final heater (13) is shut down for a CIP-procedure by closing off the respective entry valve (133) and exit valve (135) comprised in the first sequence (I) of process elements. This is done while allowing the food product (11) alternative passage (during CIP of the first sequence (I)) to the cooler (14) through the parallel sequence (III) of process elements; by opening the respective entry valve (233) and exit valve (235) comprised in the parallel sequence (III) of process elements.

Cleaning-in-place of the first sequence (I) during its disconnect from the matter flow of the processing line (30) is effectuated in such manners which are normal in the art by allowing cleaning agents and flushing agents to enter the first sequence (I) through a CIP-inlet (131) by opening the CIP-inlet valve (134) and allowing the cleaning agents to exit the first sequence (I) through a CIP-outlet (132) by opening the CIP-outlet valve (136). After cleaning the CIP-inlet (134) and CIP-outlet (136) valves are shut, thus isolating the CIP-system from the processing line (30) and first sequence (I) once more.

When, accordingly, the first sequence (I) of process elements, and in particular the first final heater (13), have been adequately cleaned by the CIP-procedure chosen, the parallel sequence (III) of process elements can be disconnected from the matter flow of the food product (11) through the processing line (30) in the same manner as described for the first sequence (I), and subsequently submitted to CIP as described above. Thereupon, the first sequence (I) can be coupled into the matter flow again following the above described procedure for coupling the parallel sequence (III) into the matter flow of the food product through the processing line (30). Depending on the design of the processing line (30), the second final heater (23) and the parallel sequence (III) can be operated either only for sufficient time to allow the first sequence (I) and first final heater (13) to undergo CIP; or the two sequences (I,III) of process elements can share the workload in the processing line (30) up to and including equal sharing, such that each sequence (I,III) operates 50% of the uptime of the processing line (30).

The effect of operating the processing line (30) according to the above detailed method is, that the overall uptime of the processing line (30) no longer is dependent on the process element and/or processing equipment with the shortest uptime, but rather becomes dependent on process elements and/or processing equipment with longer, usually much longer, uptimes compared to the process element and/or processing equipment with the shortest uptime.

In the exemplified food processing line (30) of the invention, a flash cooler (14) is localized after the two aforementioned sequences (I,III) have been reunited into one process line, the flash cooler (14) having a vapor exit (17) and an exit for the treated product (15). The flash cooler (14) can be replaced by a heat exchanger for cooling, typically, when the final heaters are operating at pasteurizing temperatures, or it can be augmented with further coolers, in the form of heat exchangers, if the exit temperature of the treated product from the flash cooler (14) is too high for packaging. This latter embodiment is common when sterilizing the food product (11) and is exemplified in FIG. 5 for a specific embodiment of the invention used to test the inventive concept in the examples.

FIGS. 4 and 5 detail specific embodiments of the generalized food processing line (30) of the invention, wherein the food processing lines (40,50) are pasteurizing (40) or sterilizing (40,50) food processing lines for treatment of a liquid food product (11), wherein the food processing line of FIG. 4 can be both.

In the setup of FIG. 4, a liquid food product (11) is comprised in a feed tank (41), from where it is pumped (471) to an indirect heater (42), e.g. in the form of a tubular or plate heat exchanger. Optionally, after the indirect heater (42) a booster pump (472) can be located. At a point on the food processing line (40) after the indirect heater (42) and, when present, after the optional booster pump (472), the food processing line (40) is split into the aforementioned to parallel sequences (I,III) of process elements, wherein each sequence can be valved (133,135,233,235) off from and opened to as detailed above. CIP-entry valves (134,234) and exit valves (136,236) as detailed above are further provided on the respective sequences (I,III) as described above.

When the food processing line (40) is a pasteurizing food processing line, the indirect heater (42) heats the food product (11) to a first temperature, which is not a pasteurizing temperature, and when the food processing line (40) is a sterilizing food processing line, the indirect heater (42) preferably heats the food product to a first temperature, which is a pasteurizing temperature. When the food processing line (40) is a pasteurizing food processing line (40), the final heaters (13,23) are usually tubular or plate heat exchangers, e.g. scraped plate heat exchangers, and when the food processing line (40) is a sterilizing food processing line (40), the final heaters (13,23) preferably are direct steam heaters, particularly preferred either injection (direct steam injection, DSI injection) or infusion (direct steam infusion), direct steam heaters, both of which options are preferred.

A flash cooler (44) is located after the two sequences (I,III) have been reunited as detailed above. Vapor (17) can be led from the flash cooler (44) to a condenser (46) and pumped (474) for further uses or disposed as waste, while the treated product (15) is pumped (473) via an indirect cooler (441) to a filling station (45) before exiting the food processing line (40).

The food processing line (40) exemplified in FIG. 4 is particular suitable for sterilizing a food product (11), in particular milk, juice, soy milk or such like products. But as detailed above, with minor changes to the process equipment, the food processing line (40) will be equally suitable for pasteurizing a food product (11) while executing the method on the invention on the food processing line (40).

FIG. 5 details the food processing line (50) which was used to perform the below described experiments. For clarity, the CIP-system and the CIP-entry valves (134,234) have not been detailed, however they are as detailed in FIGS. 3 and 4.

In the Figure, the food product (11), in the experiments skim milk, is held in an optional feed tank (51) prior to sterilization. From the optional feed tank, the food product (11) is pumped (571) to a pre-heater (52), which in the example and in the experiments, heats the food product to a pasteurizing temperature for milk (75° C.), thereby readying the milk for the subsequent sterilization heating. A three-way valve (58) has replaced the two individual valves (133,233) detailed in FIGS. 3 and 4 as entry point to the two respective sequences (I,III). In the sequences (I,III) the final heater (13) of this embodiment is a composite of a direct steam infusion heater (13a) (APV instant Infusion, c.f. WO 96/16556) and a subsequent holding cell (13b) wherein the total holding time for the milk of the experiments is on the order of 7 sec at 146° C. for the actual sterilization. Ball valves (136,236) mark the exit points for the CIP-liquids used in the experiments, and two back pressure valves (135,235) complete the aforementioned sequences (I,III) and reunites the food processing line (50). As detailed above, it is generally preferred to use backpressure valves as the valves (135,235) and further this is recommended when a three-way valve (58) is used as in the present embodiment.

Due to the high sterilizing temperatures (146° C.) employed in the experiments, the flash cooler (54) has been augmented with a pair of subsequent, but optional, indirect coolers (541,542) and with a centrifugal pump (573), located directly after the flash cooler (54), for providing the necessary flow capacity after pressure loss in the flash cooler (54). The flash cooler (54) cools the milk to about 64° C. and the subsequent indirect coolers (541,542) cool to a final product temperature, in the experiments 20° C. An optional filling station (55) is arranged at the end of the food processing line (50) to deliver the sterilized food product (15) to the consumer in a ready to use form, thus completing the food processing line (50).

In general, the feed tank (51) and the indirect coolers (541,542) are optional in the process line (50) of FIG. 5. Their presence in the line reflects the pilot plant setup used in the experiments, particularly regarding the use of two indirect coolers, which reflects the available heat exchangers at the pilot site for use in the experiments. In production, flash cooling capacity and the combination with the optional indirect cooler or coolers can be tailored to optimize production capacity and foot print in manners known to the skilled person, when cooling superheated, aqueous food products such as milk or juice etc.

As such and further to the above embodiments, the invention disclosed herein concern in a further embodiment:

A method of operating a food processing line (30) during a cleaning-in-place procedure comprising:

a) providing a food processing line (30) comprising a plurality of sequentially and fluidly connected process elements (12,13,23,14), at least a first and a second process element of the plurality of process elements (13,23) being substantially alike;

b) arranging the food processing line (30) to permit a food product (11) to traverse the food processing line (30) and the plurality of sequentially and fluidly connected process elements (12,13,23,14) as a matter flow, thereby converting the food product (11) into a treated product (15) in a food treatment process;

c) arranging the at least one first process element (13) of the plurality of sequentially and fluidly connected process elements (12,13,23,14) on a first sequence (I) of process elements, the first sequence (I) further comprising an entry valve (133) arranged at an entry point to the first sequence (I) and an exit valve (135) arranged at an exit point to the first sequence (I), the at least one first process element (13) arranged between the entry and the exit valves (133,135), the arrangement of entry and exit valves (133,135) so arranged on the food processing line (30) that the first sequence (I) can be valved off from and opened to the food processing line (30) and the matter flow of food product (11) during operation of the food processing line (30) by opening and closing of the entry and exit valves (133,135);

d) arranging the at least one second process element (23) of the plurality of sequentially and fluidly connected process elements (12,13,23,14) on a parallel sequence (III) of process elements, the parallel sequence (III) further comprising an entry valve (233) arranged at an entry point to the parallel sequence (III) and an exit valve (235) arranged at an exit point to the parallel sequence (III), the at least one second process element (23) arranged between the entry and the exit valves (233,235), the arrangement of entry and exit valves (233,235) so arranged on the food processing line (30) that the parallel sequence (III) can be valved off from and opened to the food processing line (30) and the matter flow of food product (11) during operation of the food processing line (30) by opening and closing of the entry and exit valves (233,235);

e) arranging the first sequence (I) of process elements and the parallel sequence (III) of process elements in parallel on the food processing line (30) such that a matter flow of food product (11) during operation of the food processing line (30) is possible through one of the sequences (I,III) when the other has been valved off from the food processing line (30);

f) further providing to each of the two sequences (I,III) of process elements a CIP-entry valve (134,234) and a CIP-exit valve (136,236) respectively arranged on each sequence (I,III) of process elements between a the entry valve (133, 233) and a the exit valve (135,235) on each respective sequence (I,III), the respective first or second process element (13,23) arranged between the respective CIP-entry valve (134,234) and the respective CIP-exit valve (136,236);

the method further comprising:

g) prior to executing the food treatment process on the food processing line (30), valving off from the food processing line (30) the parallel sequence (III) of process elements and leaving the first sequence (I) of process elements open for passage of a matter flow of the food product (11);

h) executing the food treatment process on the food processing line (30) thereby converting the food product (11) into a treated product (15) in the food treatment process;

i) switching after a time period of executing the food treatment process, concurrently during execution of the food treatment process, the matter flow from passage of the first sequence (I) to passage of the parallel sequence (III), thereby replacing the first sequence (I) by the parallel sequence (III) in the food processing line (30) concurrently during the execution of the food treatment process, by valving off the first sequence (I) from the food processing line (30) and concurrently opening the parallel sequence (III) to the food processing line (30); and j) while the first sequence (I) is valved off from the food processing line (30) executing a cleaning-in-place procedure on the first sequence (I).

In one embodiment, a method wherein steps i) and j) are repeated until the food processing line (30) is halted and/or the food treatment process is terminated.

In one embodiment, a method wherein the food processing line (30) is a heat treatment system for treating or sterilizing a food product at a temperature above 120° C.

In one embodiment a method where, in the food processing line (30), the food product (11) is first submitted to preheating in a preheater (12) prior to being submitted to a high temperature treatment in either of the first or the parallel sequences (I,III).

In one embodiment a method, wherein the first and the second process elements of the plurality of process elements (13,23) are a first final heater (13) and a second final heater (23).

In one embodiment a method, wherein the first final heater (13) and the second final heater (23) are both direct steam heaters and the food processing line (30) further comprises at least one flash cooler (14) arranged on the food processing line (30) after the first and the second final heaters (13,23).

In a preferred embodiment of the invention as disclosed in FIGS. 3 and 4, there is disclosed:

A method of operating a food processing line (30) during a cleaning-in-place procedure comprising:

a) providing a food processing line (30) comprising a plurality of sequentially and fluidly connected process elements (12,13,23,14), the plurality of sequentially and fluidly connected process elements (12,13,23,14) comprising a pre-heater (12), a first direct steam heater (13), a second direct steam heater (23), and a flash cooler (14), the direct steam heaters (13,23) being substantially alike, the pre-heater (12), direct steam heaters (13,23) and the flash cooler (14)

arranged sequentially on the food processing line (30) with the direct steam heaters (13,23) arranged after the pre-heater (12) but before the flash cooler (14);

b) arranging the food processing line (30) to permit a milk derivative (11) to traverse the food processing line (30) and opening the plurality of sequentially and fluidly connected process elements (12,13,23,14) as a matter flow, thereby converting the milk derivative (11) into a heat treated milk derivative (15) in a high temperature milk derivative sterilization process;

c) arranging the first direct steam heater (13) on a first sequence (I) of process elements, the first sequence (I) further comprising an entry valve (133) arranged at an entry point to the first sequence (I) and an exit valve (135) arranged at an exit point to the first sequence (I), the first direct steam heater (13) arranged between the entry and the exit valves (133,135), the arrangement of entry and exit valves (133,135) so arranged on the food processing line (30) that the first sequence (I) can be valved off from and opened to the food processing line (30) and the matter flow of the milk derivative (11) during operation of the food processing line (30) by opening and closing of the entry and exit valves (133,135);

d) arranging the second direct steam heater (23) on a parallel sequence (III) of process elements, the parallel sequence (III) further comprising an entry valve (233) arranged at an entry point to the parallel sequence (III) and an exit valve (235) arranged at an exit point to the parallel sequence (III), the second direct steam heater (23) arranged between the entry and the exit valves (233,235), the arrangement of entry and exit valves (233,235) so arranged on the food processing line (30) that the parallel sequence (III) can be valved off from and reopened to the food processing line (30) and the matter flow of milk derivative (11) during operation of the food processing line (30) by opening and closing of the entry and exit valves (233,235);

e) arranging the first sequence (I) of process elements and the parallel sequence (III) of process elements in parallel on the food processing line (30) such that a matter flow of milk derivative (11) during operation of the food processing line (30) is possible through one of the sequences (I,III) when the other has been valved off from the food processing line (30);

f) further providing to each of the two sequences (I,III) of process elements a CIP-entry valve (134,234) and a CIP-exit valve (136,236) respectively arranged on each sequence (I,III) of process elements between a the entry valve (133, 233) and a the exit valve (135,235) on each respective sequence (I,III), the respective first or second direct steam heaters (13,23) arranged between the respective CIP-entry valve (134,234) and the respective CIP-exit valve (136,236);

the method further comprising:

g) prior to executing the high temperature milk derivative sterilization process on the food processing line (30), valving off from the food processing line (30) the parallel sequence (III) of process elements and leaving the first sequence (I) of process elements open for passage of a matter flow of the milk derivative (11);

h) executing the high temperature milk derivative sterilization process on the food processing line (30) thereby converting the milk derivative (11) into a heat treated milk derivative (15) in the high temperature milk derivative sterilization process;

i) switching after a time period of executing the high temperature milk derivative sterilization process, concurrently during execution of the high temperature milk derivative sterilization process, the matter flow from passage of the first sequence (I) to passage of the parallel sequence (III), thereby replacing the first sequence (I) by the parallel sequence (III) in the food processing line (30) concurrently during the execution of the high temperature milk derivative sterilization process, by valving off the first sequence (I) from the food processing line (30) and concurrently opening the parallel sequence (III) to the food processing line (30); and j) while the first sequence (I) is valved off from the food processing line (30) executing a cleaning-in-place procedure on the first sequence (I).

Figure 6:
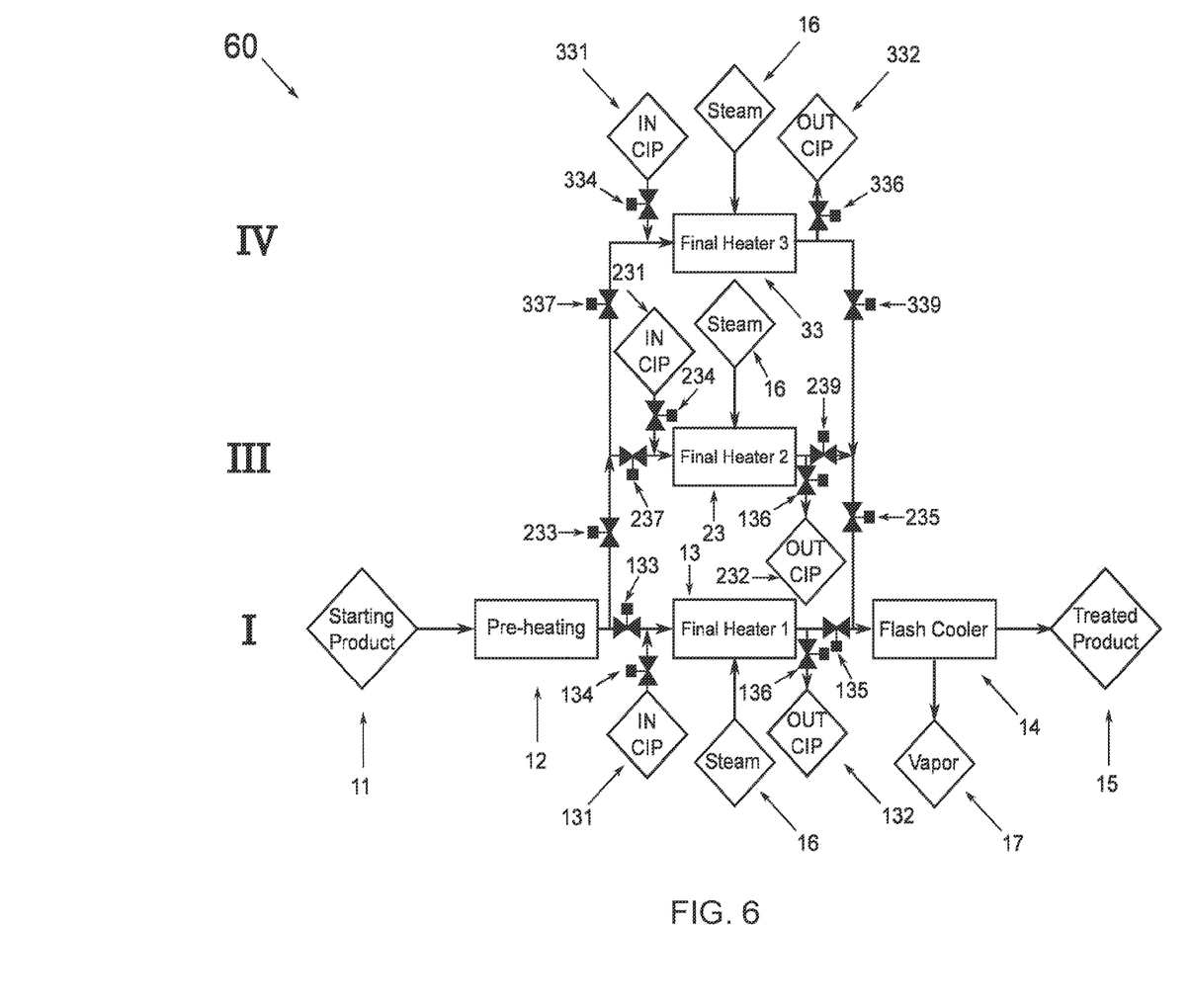
FIG. 6: High temperature food processing line of the invention in a further embodiment
Figure 7:
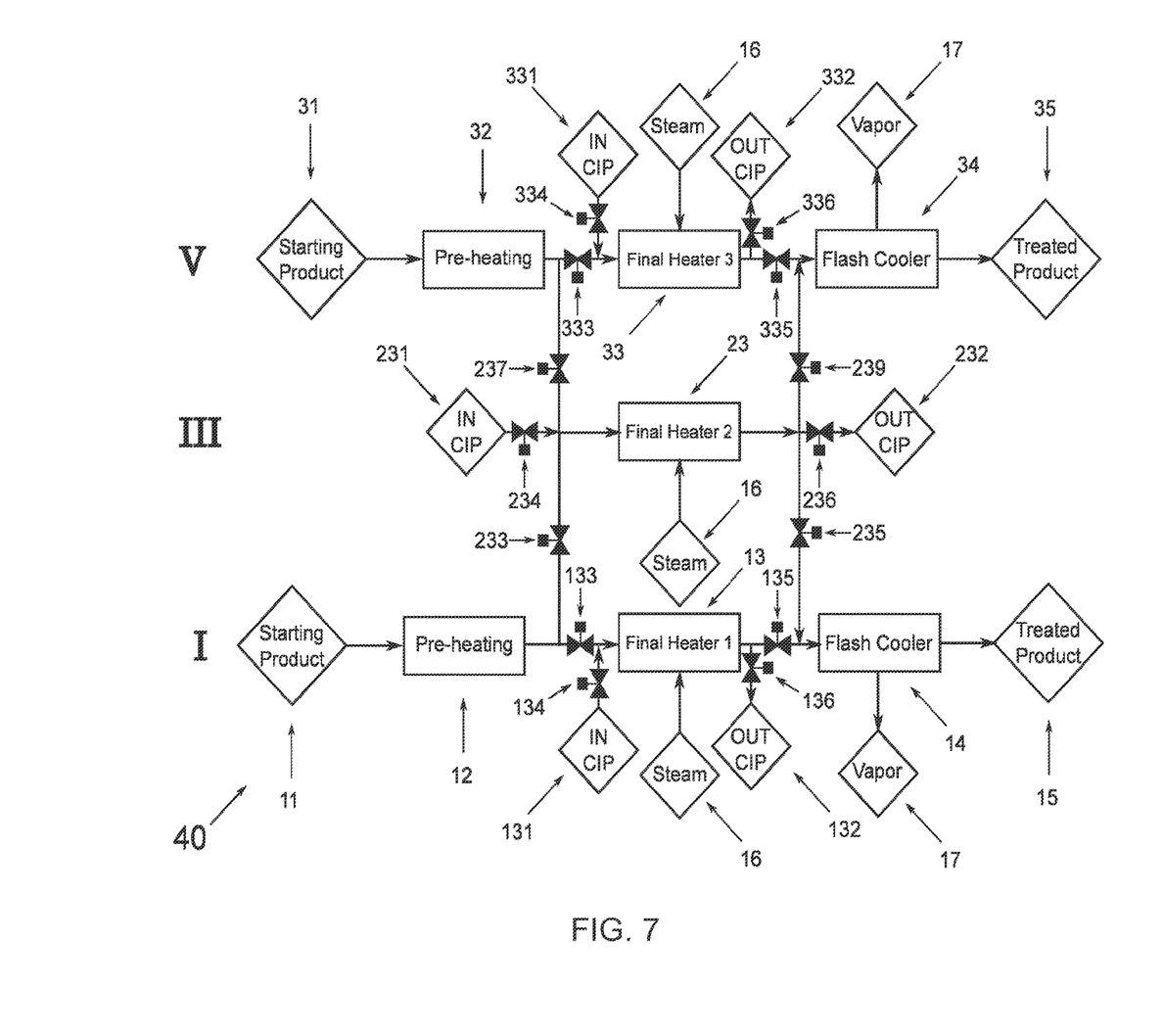
FIG. 7: High temperature food processing line of the invention in a further embodiment

FIGS. 6 and 7 detail further developments of the inventive concept.

FIG. 6 details a production line (60) as detailed above comprising a further sequence (IV) arranged in parallel on the production line (60) with the respective first and parallel sequences (I,III), the further sequence (IV) comprising entry and exit valves (337,339) and CIP-entry and exit valves (334,336) arranged there between and a final heater 3 (33) arranged between the CIP-entry and exit valves. A setup such as detailed in FIG. 6 is useful when cleaning times are longer than fouling times, such that two parallel sequences (I,III) cannot guarantee continuous operation. In operation, though, the cleaning times will generally always be shorter than the fouling times in a well-designed production plant.

FIG. 7 details, however, an improved use of the system detailed in FIG. 6. As mentioned, the cleaning times are usually shorter, even significantly shorter, than the time to fouling. In the below experiments, cleaning time for the test setup was 90 sec. after production runs of 25 min, so the doubling of the final heater capacity may lead to lowered utilization of one or both final heaters (13,23). It can therefore be advantageous for two production lines (I,V) to share a common parallel sequence (III), whereby load times on the common parallel sequence (III) is increased. E.g. in the production line (20) detailed in WO 2004/077968, where the two final heaters (13,23) both must remain online at all times due to the separator (18), so sharing a common parallel sequence (III) would allow continued operation also of this type of sterilization production line during CIP of one of the final heaters (13,23).

For the production line of WO 2004/077968, where one final heater receives a fraction of juice with a high dry matter content and the other receives a fraction of juice with a low dry matter content, it is likely to expect that the final heater receiving the fraction with the high dry matter content will be in need of cleaning more often than its counterpart.

However, the setup detailed in FIG. 7 can easily accommodate this as well. In such a shared setup, the preheaters (12,32) can be different, if the treatment temperature of the two production lines (I,V) require different temperatures, or they can be combined into a single unit, if the system requirements so permit.

According to the present invention there is therefore also disclose a food sterilization line (40,50), said food sterilization line (40,50) comprising:

a plurality of operatively, sequentially arranged and fluidly connected process elements (42,52,13,23,44,54) comprising a first and second direct steam heater (13, 23) for sterilizing a pumpable food product (11) at a temperature between 120° C. and 160° C. and operatively arranged in parallel on, respectively, a first sterilizing sequence (I) and a parallel sterilizing sequence (III) of process elements on said food sterilization line (40,50), such that said first sequence (I) comprising said first direct steam heater (13) can be valved (133,135) off from or opened to said food sterilization line (40,50), when said parallel sequence (III) comprising said second direct steam heater (23), respectively is oppositely valved (234,235) off from or opened to said food processing line (30);

wherein each of said two sequences (I,III) comprises inlet valves (134,234) and outlet valves (136,236) arranged around all process elements (13,23) on a sequence (I;III) for permitting cleaning agents for use in a cleaning-in-place procedure entry to and exit from a respective sequence (I,III), while a said respective sequence (I,III) is valved off from food sterilization line (40,50);

wherein said respective sequences (I,III) divert from and reunite to said food sterilization line (40,50) at said respective inlet (134,234) and outlet valves (136,236);

said food sterilization line (40,50) further comprising:

a pre-heater (42,52) operatively arranged on said food sterilization line (40,50) upstream from said sequences (I,III) before said sequences divert from said food sterilization line (40,50); and a flash cooler (44,54) operatively arranged on said food sterilization line (40,50) downstream from said sequences (I,III) after said sequences reunite with said food sterilization line (40,50);

characterized in that:

when one sequence (I,III) is available as an operative sterilizing sequence for the food sterilization process, the other sequence (I,III) is not available as an operative sterilizing sequence for the food sterilization process.

In a further embodiment of the food sterilization line (40,50), it further comprises a feed tank (41,51) operatively arranged on said food sterilization line (40,50) upstream from said pre-heater (42,52).

In a further embodiment of the food sterilization line (40,50), it further comprises a filling station (45,55) arranged at a downstream end of said food sterilization line (40,50).

In a further embodiment of the food sterilization line (40,50), it further comprises at least one indirect cooler (441,541,542) arranged on said food sterilization line (40,50) after said flash cooler (44,54) and before, when present, said filling station (45,55).

Other embodiments of the food sterilization line (40,50), the food sterilization line (40,50) have been detailed more in-depth in the discussion of FIGS. 4 and 5, wherein the exemplary food sterilization lines (40,50) of the invention have been discussed and the embodiments thereof.

In a further embodiment of the food sterilization line (40,50), it further comprises a controller for executing a method according to any of the embodiments detailed in the present disclosure. Such controllers are generally known to the skilled person and programming a such controller to execute a method of the present invention is within the skills of the skilled person, once knowledge of the methods of the invention has been imparted to the same skilled person.

EXAMPLES

Example 1

The purpose of the test was to prove the feasibility of preparing aseptic samples while changing from one direct steam final heater or DSI-injector (Direct Steam Injection) to another during continuous sterile production.

A full sterilization line (as in FIG. 5), with one common pre-heater and with two final direct steam heaters in parallel, the lines feeding into one common flash cooling vessel and further to a sterile cooling heat exchanger and a sterile packing machine. Milk samples for sterility testing were taken from samples packaged by the packaging machine.

12 kg skimmed milk powder (Arla Foods) was dissolved in 100 kg tap water (55° C.) (Flex-Mix Liquiverter) and hydrated for 30 minutes. Control samples were removed prior to passage of the processing line.

The plant was a 100 l/h SPP pilot UHT plant, with plates for preheating and cooling and mounted with double final heater steam injectors (first and second injectors) (Model: 17 mm/2.66 mm). After preparation, samples were filled in 5 l aseptic bags with Rapak intasept 2200 filler.

Sterilization was run at 145° C. by passing the milk through the first injector (DSI), while access to the second injector was denied, after which the second injector was switched into the flow path, while denying access to the first injector, and the milk sterilized on the second injector at 145° C. The milk was run for 25 min past each injector.

Test samples (10) from each injector were incubated at 30° C. for 3 days and pH was measured for each sample (pH=6.62). The un-pasteurized feed sample was incubated under the same conditions, 30° C. for 3 day and pH measured, pH=4.63. The sterilized samples showed no drop in pH, compared to fresh milk (pH around 6.62), thereby confirming that both sets of milk samples was sterile.

The test proved the feasibility of inline switching between two sterilization lines without overall loss of sterility during continuous sterile milk production.

Example 2

The test plant of Example 1 was used for testing the inline cleaning procedure after running the experiments of Example 1.

Lye (27.5% NaOH) was mixed with process water at 70° C. to a solution of 2.5% lye. The CIP-solution was poured into balance tank for a supply of cleaning agents in the CIP-procedure.

In a first test, the CIP-solution was pumped through the first DSI-injector of Example 1 at 55° C. and 150 L/h, and the conductivity of the CIP-solution was measured at the point of CIP-solution exit from the sequence of the production line comprising the first DSI-injector.

The time for the CIP-solution at exit to revert to the conductivity of the pure 2.5% lye solution was 90 s, corresponding to 3.75 l of CIP-solution having been pumped through the sequence of the production line comprising the first DSI-injector before returning to the initial conductivity.

In a second test, the CIP-solution was pumped through the entire production line via the second DSI-injector of Example 1 at 55° C. and 150 L/h, and the conductivity of the CIP-solution was measured at the point of CIP-solution exit from the production line comprising the second DSI-injector.

The time for the CIP-solution at exit to revert to the conductivity of the pure 2.5% lye solution was 300 s, corresponding to 12.5 l of CIP-solution having been pumped through the production line comprising the second DSI-injector before returning to the initial conductivity.

Following the method of the invention, the time to clean and the consumption of CIP-solution were both improved by a factor of 3.3 over the prior art solutions.

CLOSING COMMENTS

The term "comprising" as used in the claims does not exclude other elements or steps. The term "a" or "an" as used in the claims does not exclude a plurality. A single processor or other unit may fulfill the functions of several means recited in the claims.

Although the present invention has been described in detail for purpose of illustration, it is understood that such detail is solely for that purpose, and variations can be made therein by those skilled in the art without departing from the scope of the invention.

The invention claimed is:

1. A food sterilization line comprising:
a plurality of operatively, sequentially arranged and fluidly connected process elements comprising a first and second direct steam heater for sterilizing a pumpable food product at a temperature between 120° C. and 160° C. and operatively arranged in parallel on, respectively, a first sterilizing sequence (I) and a parallel sterilizing sequence (III) of process elements on said food sterilization line, such that said first sterilizing sequence (I) comprising said first direct steam heater can be valved off from or opened to said food sterilization line, when said parallel sterilizing sequence (III) comprising said second direct steam heater, respectively is oppositely valved off from or opened to said food processing line;
wherein each of said first and parallel sterilizing sequences (I, III) comprises inlet valves and outlet valves arranged around all process elements on a sterilizing sequence (I; III) for permitting cleaning agents for use in a cleaning-in-place procedure entry to and exit from a respective sterilizing sequence (I, III), while said respective sterilizing sequence (I, III) is valved off from the food sterilization line;
wherein said respective sterilizing sequences (I, III) divert from and reunite to said food sterilization line at said respective inlet and outlet valves;
said food sterilization line further comprising:
a pre-heater operatively arranged on said food sterilization line upstream from said first and parallel sterilizing sequences (I, III) before said first and parallel sterilizing sequences divert from said food sterilization line; and
a flash cooler operatively arranged on said food sterilization line downstream from said first and parallel sterilizing sequences (I, III) after said first and parallel sterilizing sequences reunite with said food sterilization line;
characterized in that:
when one of said first and parallel sterilizing sequences (I, III) is performing an operative sterilizing sequence for the food sterilization line, the other of said first and parallel sterilizing sequences (I, III) is performing said cleaning-in-place procedure by circulating the cleaning agents and is not available as an operative sterilizing sequence for the food sterilization line and wherein said first and parallel sterilizing sequences are alternatingly operated between the operative sterilizing sequence and the cleaning-in-place procedure to continuously operate the food sterilization line, wherein said first and parallel sterilizing sequences (I, III) do not comprise a pre-heater and/or a cooler.

2. The food sterilization line according to claim 1, further comprising a feed tank operatively arranged on said food sterilization line upstream from said pre-heater.

3. The food sterilization line according to claim 1, further comprising a filling station arranged at a downstream end of said food sterilization line.

4. The food sterilization line according to claim 3, further comprising at least one indirect cooler arranged on said food sterilization line after said flash cooler and before, when present, said filling station.

5. The food sterilization line according to claim 1, further comprising a controller.

6. The food sterilization line according to claim 1, wherein said first sterilizing sequence (I) consists of said first direct steam heater and wherein said parallel sterilizing sequence (III) consists of said second direct steam heater.

* * * * *